United States Patent [19]
Peredo

[11] Patent Number: 6,074,417
[45] Date of Patent: Jun. 13, 2000

[54] TOTAL MITRAL HETEROLOGOUS BIOPROSTHESIS TO BE USED IN MITRAL OR TRICUSPID HEART REPLACEMENT

[75] Inventor: Mario Osvaldo Vrandecic Peredo, Belo Horizonte, Brazil

[73] Assignee: St. Jude Medical, Inc., St. Paul, Minn.

[21] Appl. No.: 09/019,748

[22] Filed: Feb. 6, 1998

Related U.S. Application Data

[63] Continuation-in-part of application No. 08/472,956, Jun. 7, 1995, Pat. No. 5,733,331, which is a continuation-in-part of application No. 08/313,406, Sep. 27, 1994, abandoned, which is a continuation of application No. 07/976,468, Nov. 16, 1992, abandoned.

[51] Int. Cl.$^7$ ...................................................... A61F 2/00
[52] U.S. Cl. ................................................................ 623/2
[58] Field of Search ........................................ 623/2, 900

[56] References Cited

U.S. PATENT DOCUMENTS

| | | | |
|---|---|---|---|
| 3,130,418 | 4/1964 | Head et al. | 3/1 |
| 4,035,849 | 7/1977 | Angell et al. | 3/1.5 |
| 4,261,342 | 4/1981 | Aranguren Duo | 623/2 |
| 4,769,032 | 9/1988 | Steinberg | 623/2 |
| 4,960,424 | 10/1990 | Grooters | 623/2 |
| 5,156,621 | 10/1992 | Navia | 623/2 |
| 5,197,979 | 3/1993 | Quintero | 623/2 |
| 5,306,296 | 4/1994 | Wright | 623/2 |
| 5,336,258 | 8/1994 | Quintero et al. | 623/2 |
| 5,415,667 | 5/1995 | Frater | 623/2 |
| 5,554,184 | 9/1996 | Machiraju | 623/2 |
| 5,824,067 | 10/1998 | Gross | 623/2 |

FOREIGN PATENT DOCUMENTS

| | | |
|---|---|---|
| 3614292 | 11/1987 | Germany . |
| 4234127 | 5/1994 | Germany . |

OTHER PUBLICATIONS

"New Horizons and the Future of Heart Valve Bioprosthesis" by, Vetter et al., First Edition, 1994, pp. 93–104.

"Anatomically Complete Heterograft Mitral Valve Substitute: Surgical Technical and Immediate Results" by, Peredo et al., The Journal of Heart Valve Disease, 1991, vol. 1, pp. 254–4259.

"Heterologous Mitral Valve Transplant, New Alternative for Mitral Replacement: One Year Clinical Follow–up" by, Peredo et al., Heart Surgery 93; "Casa Editrice Scientifica Internazionale" Ed. Luigi C. D'Alessandro, Chapter 7, pp. 57–68.

(List continued on next page.)

*Primary Examiner*—Michael J. Milano
*Attorney, Agent, or Firm*—Westman, Champlin & Kelly, P.A.; Peter S. Dardi; Hallie A. Finucane

[57] ABSTRACT

The present invention relates to a heterologous total stentless mitral valve prosthesis for the use in mitral and tricuspid position which provides for better hemodynamic performance. This mitral valve prosthesis addresses the specific needs of flow and contractility, thereby prolonging durability. The heterologous total stentless mitral heart valve prosthesis of this present invention comprises one sewing ring, leaflets, and subvalvular apparatus having new chordal insertions which are fixed to or in between two heterologous pericardial patches. This heart valve prosthesis is obtained from heterologous mammals, such as swine, ovine, bovine, and moreover, the pericardial patches used may also be of synthetic material. The heart valve prosthesis presents specific design benefits from its anatomical and functional characteristics permitting chordal insertion to the papillary muscles and attachment of its sewing rim to the mitral annulus of the recipient, thereby providing for better hemodynamic performance and avoiding disfunction and dilatation of the left ventricle.

12 Claims, 7 Drawing Sheets

OTHER PUBLICATIONS

"A New Approach for Mitral Valve Replacement" by, Peredo et al., Heterologous Stentless Mitral Valve Transplant. Cor. European 3(3) 130–133, 1994.

"Porcine Stentless Mitral Heart Valve Substitute" by, Peredo et al, Short Term Clinical Data, J. Cardiovascular Surg. 1994: 35 (Suppl. 1 to No. 6): 41–5.

"Transplante De Valva Mitral Heterologo" by, Peredo et al, Nova Alternativa Cirugica: Estudo Clinico Inicial., Rev. Bras. Cir. Cardiovascular 8(2): 83–90, 1993.

TOTAL MITRAL HETEROLOGOUS BIOPROSTHESIS TO BE USED IN MITRAL OR TRICUSPID HEART REPLACEMENT

This application is a continuation-in-part of application Ser. No. 08/472,956, filed Jun. 7, 1995, U.S. Pat. No. 5,733,331, which is a continuation-in-part of application Ser. No. 08/313,406, filed Sep. 27, 1994, abandoned, which is a continuation of application Ser. No. 07/976,468, filed Nov. 16, 1992, abandoned.

FIELD OF THE INVENTION

The present invention relates to the heart valve prostheses, and more specifically, to those used in mitral and tricuspid positions, comprising a heterologous biological material total mitral valve device that may provide better durability and hemodynamic performance in mitral or tricuspid position, according to the specific requirements of flow and contractility of the left ventricle.

BACKGROUND OF THE INVENTION

Rheumatic heart disease remains endemic in the developing countries and is responsible for diseases associated with heart valves, and typically the mitral valve, affecting in general the younger population.

The functional consequences of these lesions are valvular stenosis, insufficiency or mixed lesions, and exploratory surgical treatment. Further, because of the severity of the lesions to the valve components, reconstructive valvular surgery may not be possible. In this case, substitution or valve replacement surgery by a mechanical valve or a bioprosthesis (composite of prosthetic and biological materials) may be required.

Mechanical prostheses have the advantage of better durability and the disadvantage of requiring life time anticoagulation and that in itself produces iatrogenic disease besides other complications such as hemorrhages, embolism and thromboembolism. An example of a mechanical prosthesis is shown in FIG. 1.

Bioprosthesis are made of a biological tissue mounted to a stent previously covered by a synthetic material in such a way as to provide a one way valve to reproduce to some extent the performance of a healthy human heart valve. An example of a bioprosthesis valve which operates without the subvalvular apparatus of the natural mitral valve is shown in FIG. 2. These bioprostheses have several advantages over the mechanical prostheses, such as, central flow, satisfactory hemodynamics, better quality of life, lower incidence of thromboembolism and bioprosthesis do not require the use of an anticoagulant.

The main drawback of the bioprosthesis is durability, especially in the younger population, due to the wear of the biological component, that is subject to high intraventricular pressures, and, in the case of the mitral valve; the current designs are not suitable to withstand high pressures and the specific flow pattern "VORTEX" of the left ventricle.

The natural mitral valve device includes a mitral annulus, mitral leaflets, subvalvular apparatus and the papillary muscles. The harmonic performance of this complex determines the adequacy of its intended function.

SUMMARY AND OBJECTS OF THE INVENTION

The current mitral heart valve prostheses are provided with a leaflet or disc fixed to a rigid stent or ring without the subvalvular and the papillary muscles components that are considered essential to the intended performance of the left ventricle as a unit.

The current mitral heart valve prostheses perform well as a one way valve permitting adequate flow characteristics. However, the absence of the subvalvular apparatus and papillary muscles, which are fundamental elements to the preservation of the left ventricular function, contribute with time to sequelae, such as dysfunctions and dilatation of the left ventricle.

It is the objective of the present invention to provide a more durable heterologous total stentless mitral valve prosthesis that will provide satisfactory hemodynamic performance in the mitral or tricuspid position. It is also an object of the present invention to provide a mitral valve prosthesis which complies with the left ventricular requirements of specific flow and contractility. This objective is accomplished by the heterologous total stentless mitral valve in the mitral and tricuspid positions of the present invention which has an anatomic and physiological design which provides the hemodynamic means for specific requirements of flow and contractility of the left ventricle in humans. Thus, the design avoids complications such as disfunction and dilatation of the left ventricle which thereby provides better quality of life for the recipient and durability in use.

BRIEF DESCRIPTION OF DRAWINGS

The invention is hereinafter described with reference to the accompanying drawings in which.

DETAILED DESCRIPTION OF THE INVENTION

Figure 1:
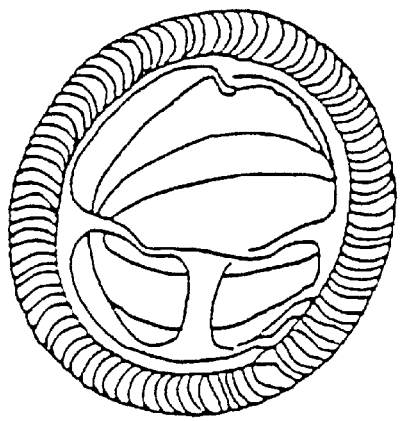
FIG. 1 illustrates a mechanical prosthesis of the prior art.
Figure 2:
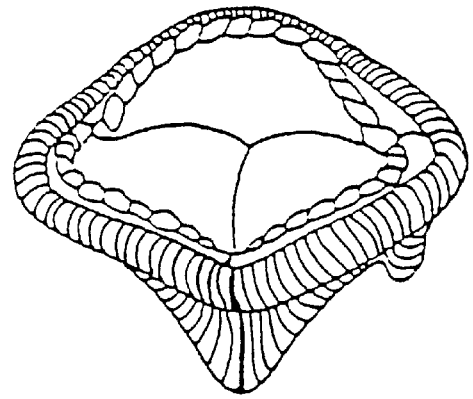
FIG. 2 illustrates a bioprosthesis of the prior art.
Figure 3:
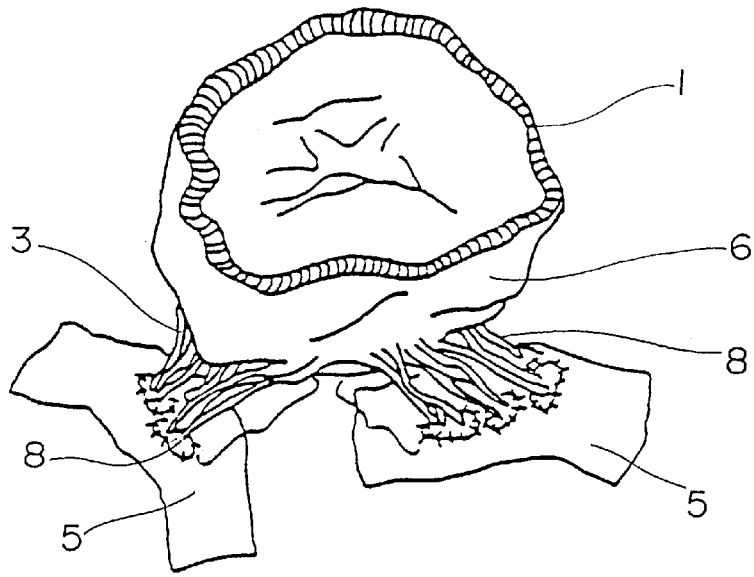
FIG. 3 illustrates a preferred embodiment of the heterologous total stentless mitral valve substitute in accordance with the teachings of the present invention for use in the mitral and tricuspid position.
Figure 4:
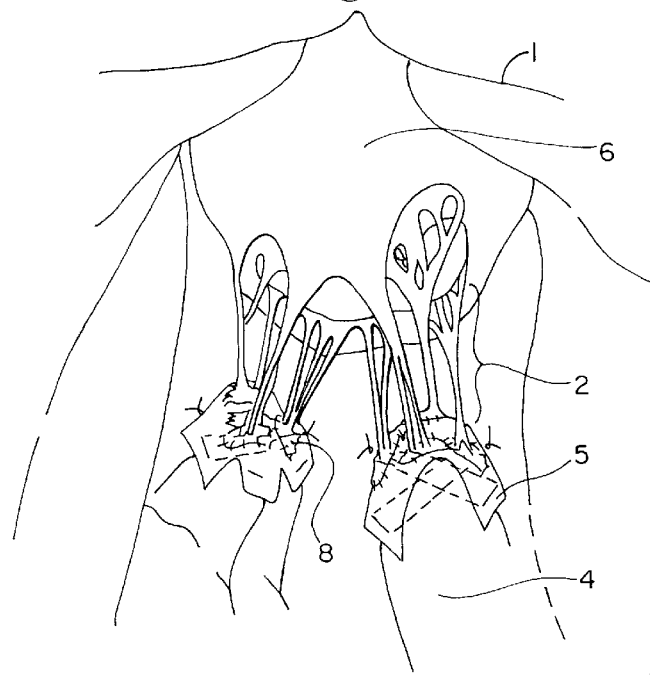
FIG. 4 illustrates the mitral valve prosthesis of FIG. 3 attached between the mitral annulus and papillary muscle of the patient.

As is shown in FIGS. 3 and 4, the heterologous total stentless mitral valve prosthesis to be used in mitral and tricuspid position of the present invention is illustrated. This mitral valve prosthesis is comprised of a mitral sewing rim (1), a complete subvalvular apparatus (2) with chordal attachments (3) which are secured naturally between mitral leaflets (6) and heterologous portions or slices (8) of the papillary muscle (chordal origin) of the animal. As shown in FIG. 4, these heterologous portions (8) of papillary muscle are fixed by suturing to a heterologous pericardial patch graft (5) or to a synthetic material to preserve its spatial geometry.

Figure 5:
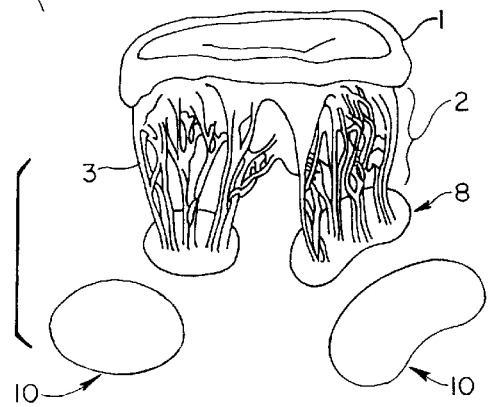
FIG. 5 illustrates the mitral valve prosthesis of FIG. 3 and pericardial tissue to be attached thereto.

The process of attaching the heterologous pericardial patches (5) to the chordal origins (8) is further described in FIGS. 5–10. FIG. 5 shows a harvested heterologous mitral heart valve; the heart valve is harvested to preserve its anatomical integrity. The pericardial tissue (10) which is used to form pericardial patch (5) is also shown in FIG. 5. The pericardial tissues (10) are formed 20% larger and in the same shape as their corresponding chordal origins (8). Since the natural chordal origin is preserved, the spatial geometry between each chordae or chordal group is not violated and the natural angle of the chordal origin (8) is maintained.

Figure 6:
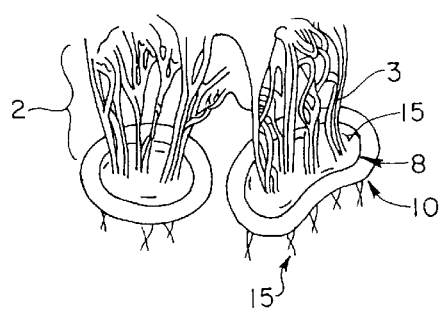
FIG. 6 illustrates the attachment of the pericardial tissue to the chordal origin by interrupted and continuous sutures.

FIG. 6 illustrates how the chordal origin or heterologous papillary muscle slice (8) is attached to the pericardial tissue (10) with interrupted and continuous sutures (15), such that the original papillary muscle angulation, as the chordae arise from the papillary slice (8), is preserved. The pericardial tissue (10) is made larger than the chordal origin (8) so the free pericardial edge can be used to anchor the mitral valve prosthesis to the patient's papillary muscle.

Figure 7:
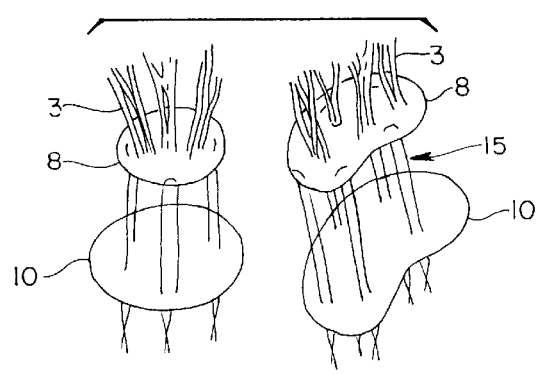
FIG. 7 further illustrates the suture attachment of the chordal origin and pericardial tissue of FIG. 6.

FIG. 7 shows the sutures (15) in more detail to demonstrate that the sutures are not attached to the delicate chordal structure so that the structural integrity of the chordae are preserved. Attaching the sutures directly to the chordal structure weakens the chordae and, therefore, lessens the durability of the mitral valve prosthesis. Thus, by attaching the sutures to the pericardial tissue, rather than each chordae, the chordal structure is not weakened as it was by the prior art attachment methods.

The pericardial tissue (10) is attached to the chordal origin (8) to preserve the original (natural) angulation of the chordal origin, which ensures that there will be uniform tension on the chordae when the mitral valve prosthesis is attached to the patient's papillary muscle. By maintaining uniform chordal tension, undue stress on the chordal origin and on the individual chordae is avoided, which lessens the chance of papillary muscle tear and makes the mitral valve prosthesis more durable. Since each mammal's mitral valve has a different spatial geometry and natural chordal origin angulation, preserving the chordal origin is the best way to ensure that these structures are preserved, so that the valve prosthesis will obtain the advantages provided by uniform chordal tension.

Figure 8:
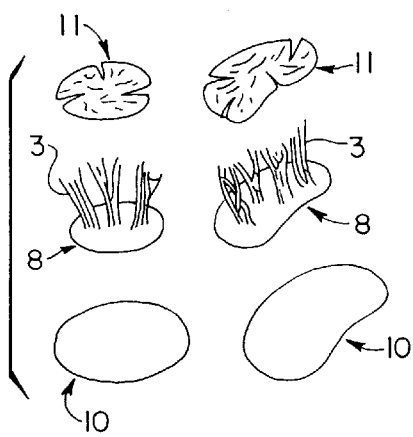
FIG. 8 illustrates the alignment of the chordal origin and the two pericardial tissues which form a patch to secure the chordal origin to the patient's papillary muscle.
Figure 9:
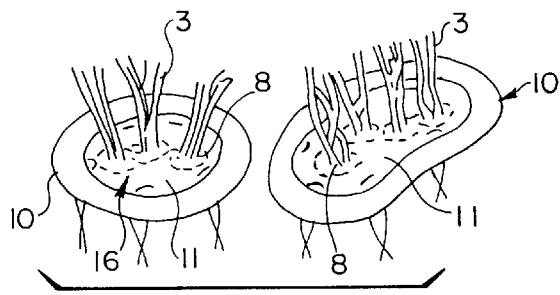
FIG. 9 illustrates the attachment of the upper (second) pericardial tissue about the chordae or chordal groups to the chordal origin and the lower pericardial tissue.
Figure 10:
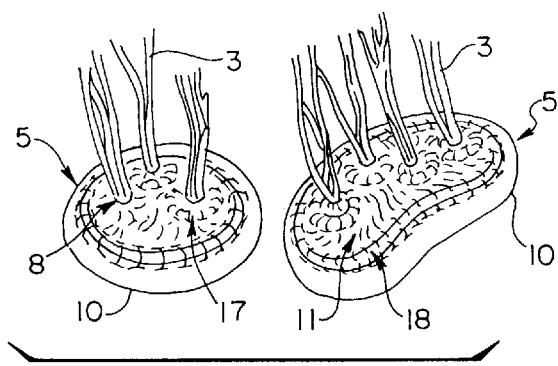
FIG. 10 illustrates the final attachment of the mitral valve prosthesis' chordal origin to the pericardial patch of the invention.

FIGS. 8–10 illustrate the attachment of an upper (second) pericardial tissue (11) to the chordal origin (8) and the pericardial tissue (10) to form the pericardial patch (5) of FIGS. 3 and 4. The second pericardial tissue (11) is of the same size or smaller than the chordal origin (8) and is divided or sliced so as to fit around each chordae or chordal group, as shown in FIG. 8. The upper pericardial tissue (11) is attached, as shown in FIGS. 8 and 9, on top of the heterologous papillary muscle slice (8) to both the chordal origin (8) and pericardial tissue (10) by continuous sutures (16). This attachment provides a well-secured chordal origin without any weakening of the chordal structure itself; the sutures are not attached to the chordal structure. The second pericardial tissue (11), like the pericardial tissue (10), is attached to the chordal origin (8) so that the spatial geometry and natural angulation of the chordal origin is preserved. Thus, the benefits provided by uniform chordal tension are maintained even after the second pericardial tissue (11) has been attached.

FIG. 10 illustrates the final affixation of the chordal origin to the pericardial patch (5). The chordae are surrounded by the upper pericardial tissue (11) so the sutures (17) do not injure the structure of the chordae and the chordal origin is attached to the pericardial tissues (10 and 11) with sutures (18) to fully respect the natural geometry of the chordal origin, thus the pericardial patch (5) is formed. The second (upper) pericardial tissue (11) acts as a collar to strengthen the chordal origin attachment and to avoid tearing of each chordae or chordal group from the thin heterologous papillary slice (8).

The free edge of the pericardial tissue (10) is maintained throughout the procedure to allow the mitral valve prosthesis to be anchored to the patient's papillary muscle. The free edge also provides a way to control alignment of the annulus (described below) and to address the issue of subvalvular height to attain consistent results. Proper alignment and the correct subvalvular height also helps to avoid undue stress and tension on the chordae and so the valve is more durable.

Figure 14B:
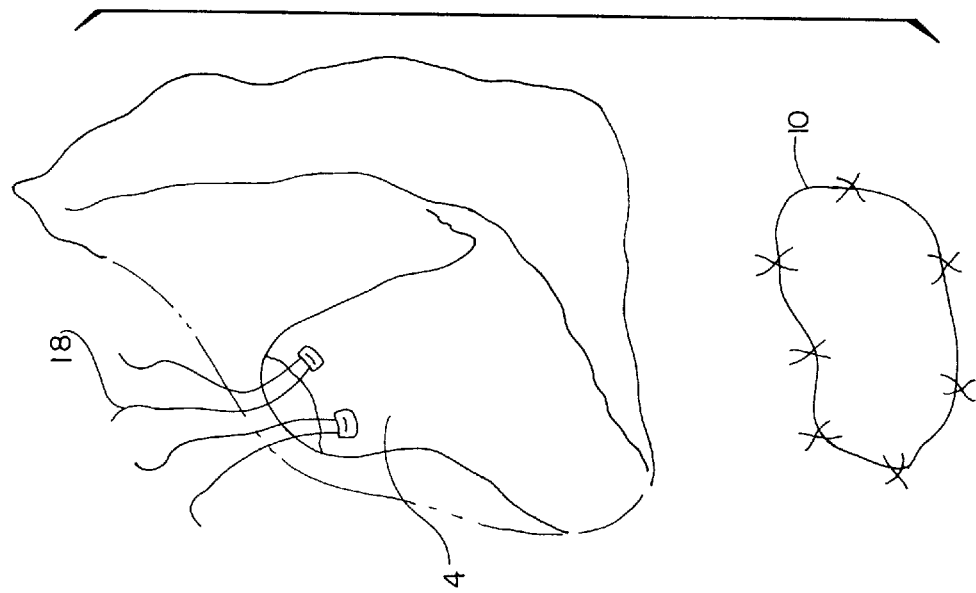
FIGS. 14A and B illustrate the correct and incorrect papillary muscle suture placement, respectively.
Figure 14A:
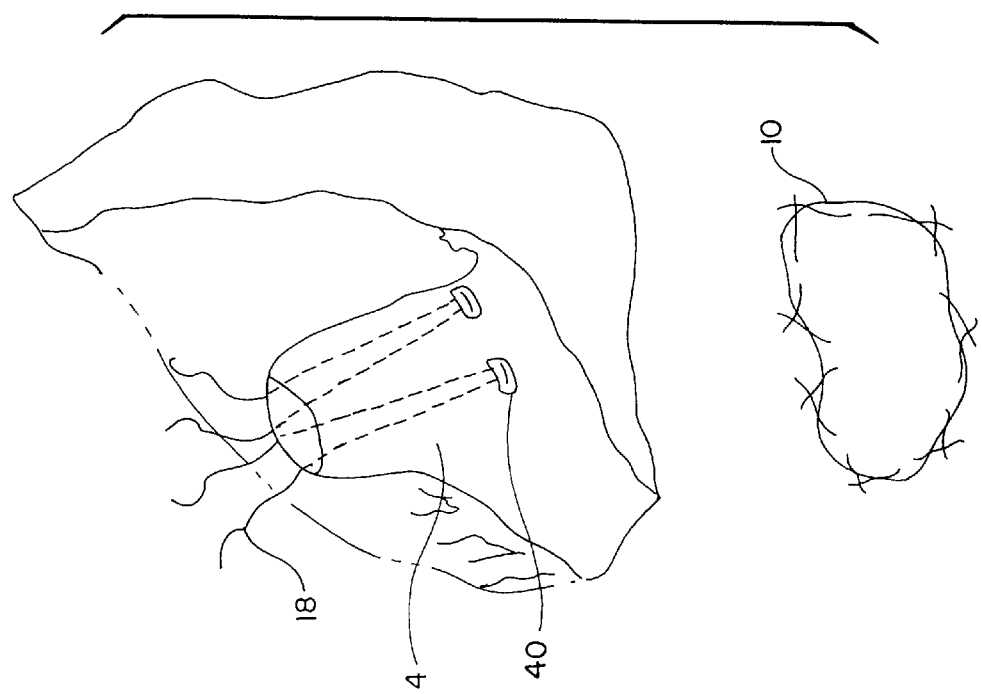
Figure 15:
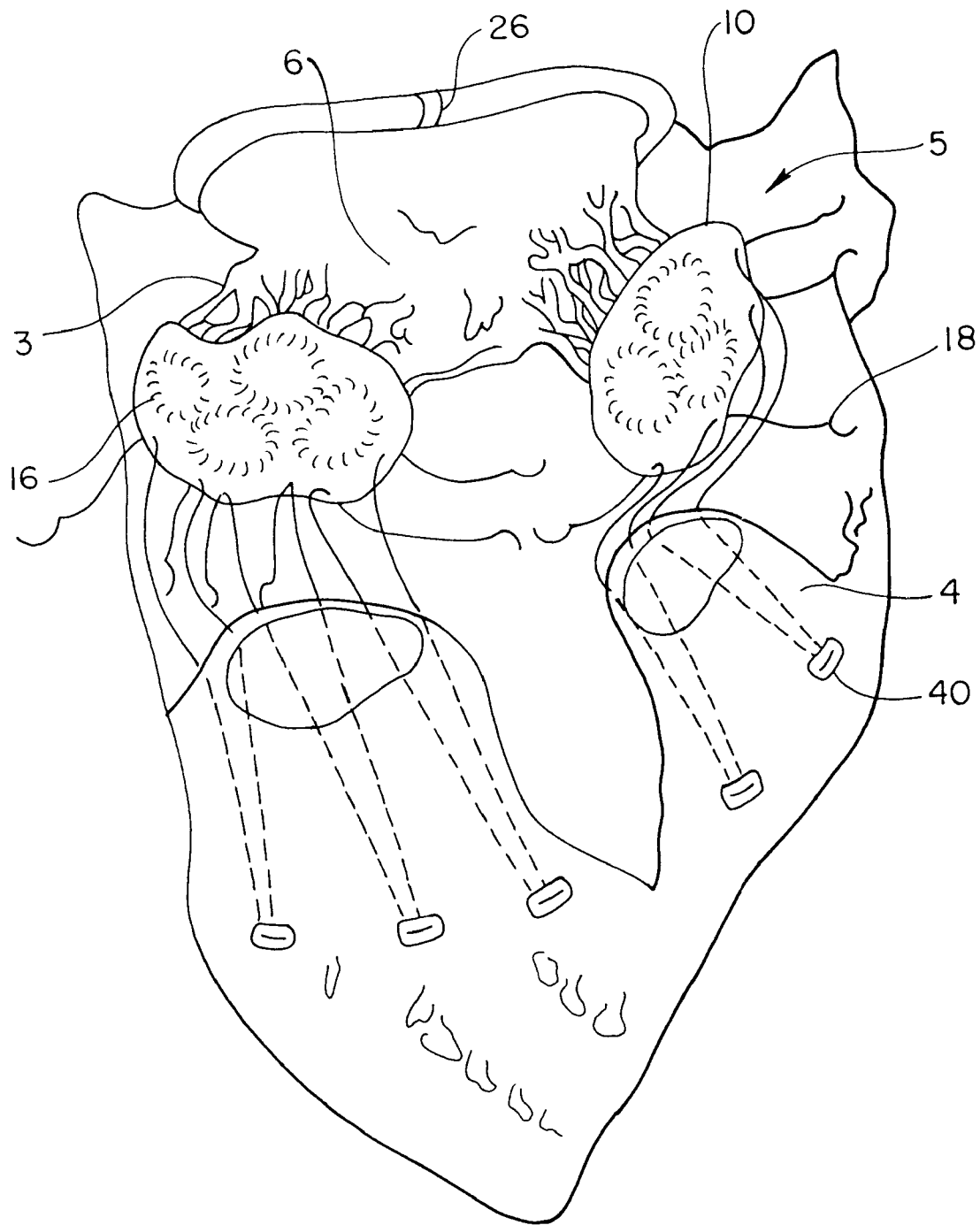
FIG. 15 illustrates the attachment of the papillary muscle sutures to the pericardial patches of the mitral valve.
Figure 16:
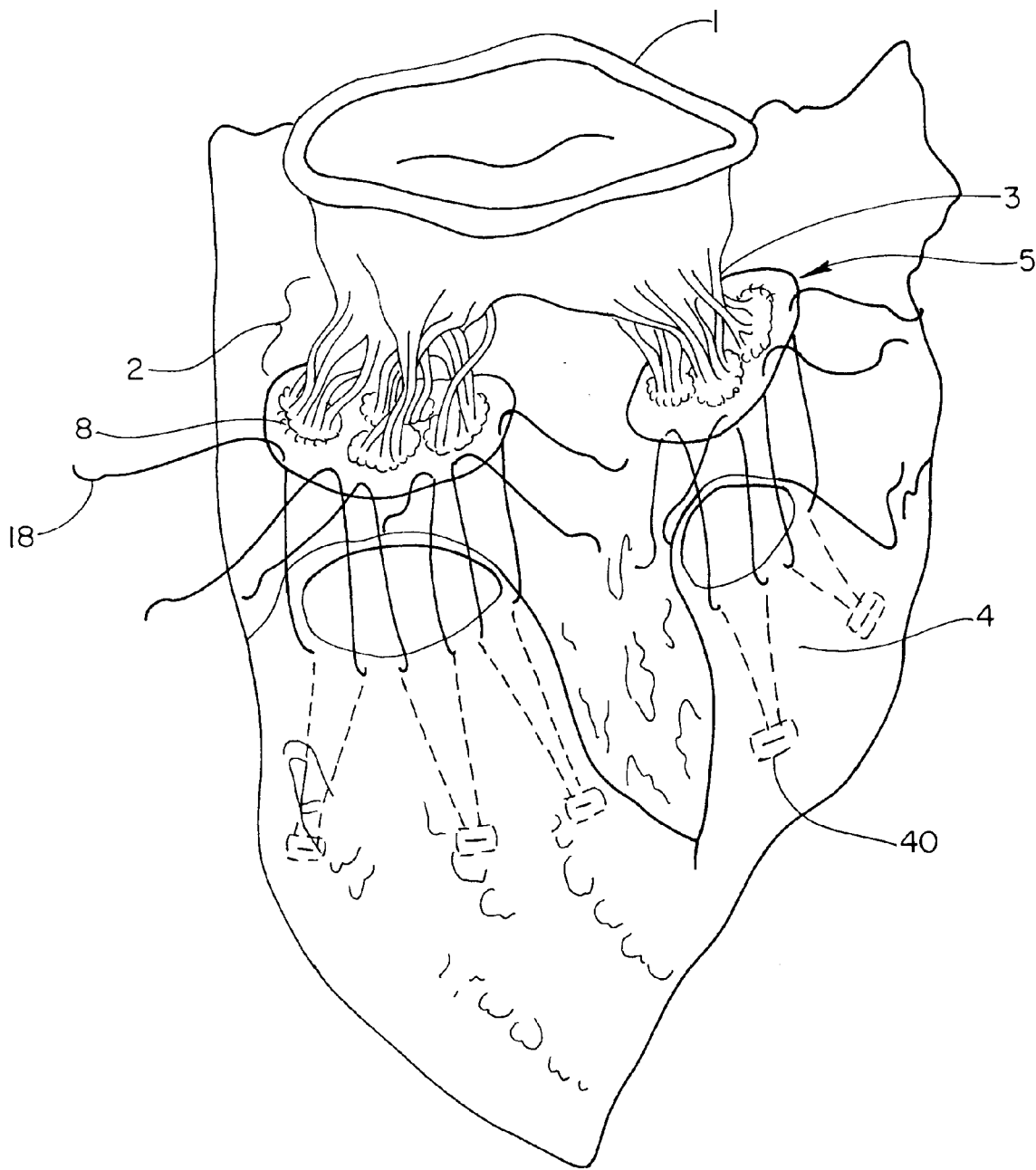
FIG. 16 is a closer view of the correct placement of the papillary muscle sutures, clearly showing the anterior to posterior angling of the sutures.

To attach the pericardial patch (5), including the chordal origin (8), to the patient's papillary muscle, it is preferred to use "U" type pledgetted sutures (18). The "U" type pledgetted sutures are squired at the origin of each papillary muscle (40) and are directed toward the papillary muscle head at a 45 degree angle towards the opposite side of the muscle, as shown in FIGS. 14–16. The pledgetted sutures must never be placed close to the head of the papillary muscle because they will tear the muscle, as illustrated in FIG. 14B. The anterior sutures anchor the posterior edge of the pericardial patch (5) and the posterior sutures anchor the anterior edge of the pericardial patch (5) to the origin of the patient's papillary muscle, as shown in FIGS. 15–16. The suture spacing is widened as they extend from the origin of the papillary muscle to encompass the circumference of the pericardial patch (5) when the sutures are attached thereto, as shown in FIG. 14A. The pledgetted sutures are attached to the free edge of the lower pericardial tissue (10) of the pericardial patch (5) so as to respect the alignment of the chordal implant in relation to the left ventricular outflow tract, as shown in FIG. 16. The alignment of the mitral valve prosthesis is perfected in relation to the X markings on the right and left trigone of the implant valve (described later).

The papillary muscle is analyzed to determine the optimal positioning of the pledgetted sutures at the posterior and anterior of the origin of the papillary muscle. It is preferred that 3 or 4 sutures be attached to each of the posterior and anterior portions of the patient's papillary muscle to ensure the proper attachment and alignment of the chordal origin (8) and the entire mitral valve prosthesis. By following this procedure, repetitive good results are possible where they have never been known before.

This heterologous device can be a native mitral valve obtained from any mammal of size, anatomy and functions similar to the human heart, including, for example, swine, ovine, bovine and others.

This heterologous mitral device is removed immediately after slaughtering of the animal by surgical technique. The entire mitral device is obtained and immersed into a balanced electrolyte, glutaraldehyde containing solution. Thereafter, the excess of muscle tissue is removed by a dissection procedure. Each procedure is performed so as to preserve the integrity of the mitral device. Continual monitoring of the quality control of each element is done daily until the proper tanning and cross linking of the tissue is obtained by the balanced electrolyte glutaraldehyde containing solution.

The posterior circumference of the patient's mitral annulus may be normal, enlarged or distended or the diameter of the mitral annulus may be moderately enlarged depending on the etiology causing the valve stenosis, insufficiency or mixed lesion. Thus, it becomes impossible to determine the correct stentless heterologous (or homologous) valve size, which is one of the reasons why previous techniques failed. If a valve with a smaller diameter is inserted into an enlarged mitral annulus, then the thin posterior annular circumference will rupture. Even if the correct valve size is selected for implant, misalignment of the valve will produce mitral leaflet prolapse which creates valve insufficiency. Prolapse can also be caused by incorrect valve sizing. Therefore, it is important not only to select the correct size valve for implant but to strengthen the posterior annular circumference and provide a systematic way to align the valve upon implantation.

Figure 11:
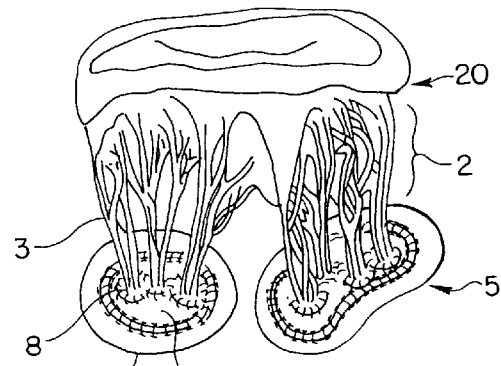
FIG. 11 shows the entire mitral valve prosthesis and illustrates the naturally weak posterior of the annulus.
Figure 12:
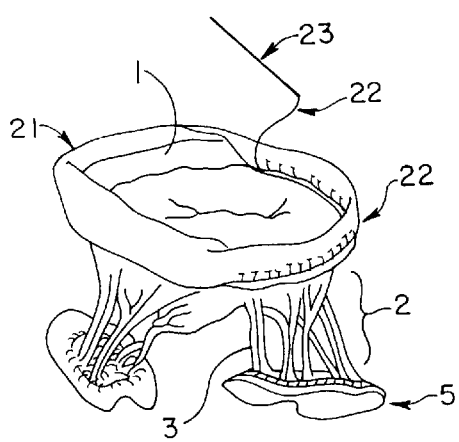
FIG. 12 illustrates the attachment of the pericardial tissue collar over the annulus of the mitral valve prosthesis.
Figure 13:
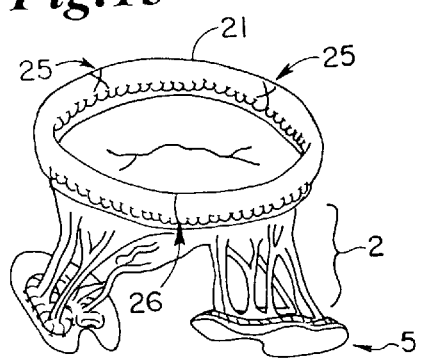
FIG. 13 illustrates the markings on the pericardial collar (sewing ring) used to select the correct size mitral valve and align the mitral valve prosthesis implant of the present invention in the patient.

FIGS. 11–13 illustrate the attachment of a pericardial tissue collar to the mitral valve sewing rim to strengthen the annulus, to provide for height adjustment of the valve in the patient and to provide a surface so that markings may be placed to determine correct sizing and alignment of the mitral valve. FIG. 11 shows the heterologous mitral valve with the chordal origin attachment of the invention. The arrow (20) points to the naturally weak posterior circumference of the annulus. The weak posterior portion represents ⅔ of the annular circumference. Once the valve is removed from the donator animal, the weak posterior portion of the annulus expands, making size determination impossible. Thus, by placing a collar around the annulus it is returned to its correct size and the left and right trigone can be marked to allow selection of a properly sized valve.

FIG. 12 shows the attachment of a pre-formed pericardial tissue (21) over the heterologous mitral annulus. The pericardial tissue is preferably approximately 1 cm in width and of the same length as the circumference of the mitral annulus, thus the mitral annulus is reinforced with approximately 50 mm of biological material on either side once the pericardial tissue is attached thereto. The attachment of the pericardial tissue (21) serves many functions, including: maintaining the natural heterologous mitral valve diameter and circumference, reinforcing the naturally weak posterior circumference of the annulus, providing a surface to secure the mitral annulus to the patient's mitral rim, permitting markings used to determine correct valve size and alignment (illustrated in FIG. 13 and described below), and providing an extra approximately 20 or 30 mm of height adjustment for valve placement.

The pericardial tissue collar (21) is attached to the mitral annulus by folding it around the annulus, thus enveloping the annulus, and using interrupted and/or continuous sutures (22) to attach the pericardial collar (21) to the mitral annulus, as shown in FIG. 12, with a needle (23). Thus, the heterologous mitral annulus is placed between the pericardium so that the above-mentioned advantages may be achieved. The new sewing ring is completely biological, with the exception of the sutures which are mono or polyfilament sutures. Alternatively, collar (21) can be a fabric sewing collar. The fabric can be woven or nonwoven. The fabric can be made from a variety of synthetic and natural polymers. Suitable polymers include polyamines (e.g., nylon), polyesters (e.g., poly(ethylene terephthalate)), polystyrenes, polyacrylates, vinyl polymers (e.g., polyethylene, expanded or nonexpanded polytetrafluoroethylene, polypropylene, and polyvinyl chloride), polycarbonates, polyurethanes, poly dimethyl siloxanes, cellulose acetates, polymethyl methacrylates, ethylene vinyl acetates, polysulfones, nitrocelluloses, collagen, elastin, silk, keratin, gelatin, polyaminoacids cellulose, starch, and combination and copolymers thereof. Preferred polymers include polyester and polytetrafluoroethylene.

FIG. 13 illustrates the markings used to determine correct valve size and provide a reference for the structural alignment required during valve implant. The X markers are placed at each of the heterologous mitral valve trigone (25). The distance between the X markers must match the patient's intertrigonal width for the valve size to be correct. The space between the left and right trigone is used because it does not vary significantly (little or no change) in either the patient or the heterologous mitral valve. The type of disease affecting the patient's mitral valve does not affect the size of this area and the anterior annular portion of the heterologous mitral valve is strong and fibrous and so does not vary in size as does the weak posterior portion. The X markings (25) are made with color sutures on the pericardial collar (21) and provide a fixed distance to determine valve size. The X markings are also used in combination with the edge of pericardial tissue (10) to help attain proper alignment of the valve upon implantation. Proper alignment of the valve prosthesis allows a uniform tension to be maintained when the chordae through pericardial patches (5) are attached to the patient's papillary muscle and thus the durability of the mitral valve prosthesis is increased.

The midpoint of the posterior annular circumference is marked "I" (26) to help determine the correct valve size and maintain alignment of the mitral valve prosthesis during implant. The "I" marking (26) further enables the valve to be implanted so that the stress force is more evenly distributed during the attachment of the valve to avoid injuring the weak posterior of the annulus.

Figure 17:
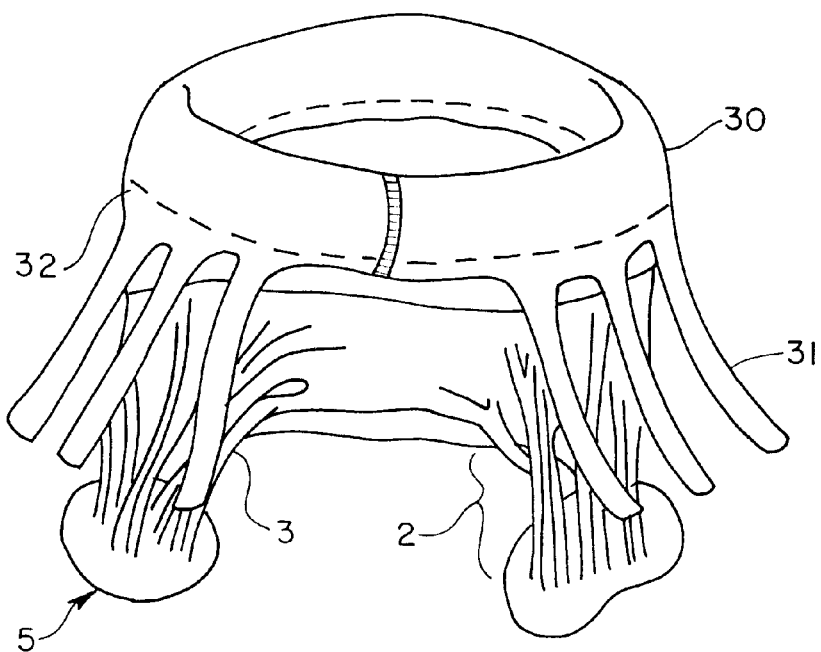
FIG. 17 illustrates another embodiment of the pericardial tissue collar of the present invention which includes naturally secured vertical strips of pericardial tissue.
Figure 18:
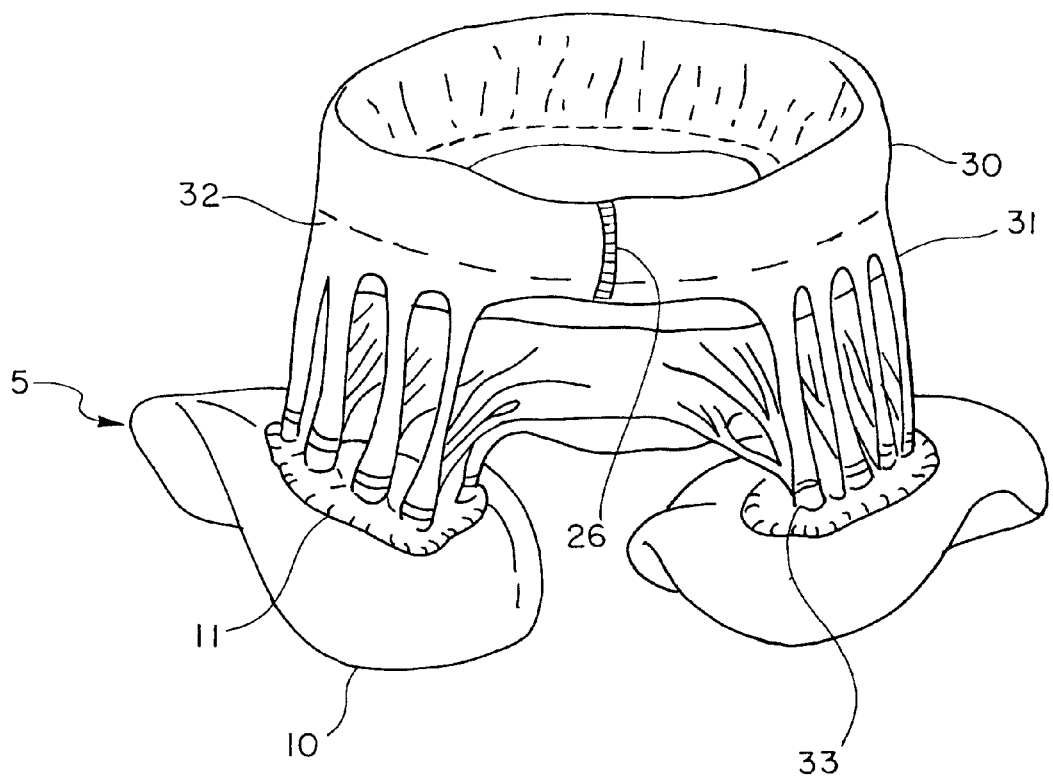
FIG. 18 illustrates the attachment of the naturally secured pericardial strips to the pericardial patches of the present invention.

As an alternative to the pericardial tissue collar shown in FIGS. 11–13, a pericardial tissue collar (30) containing naturally secured vertical pericardial strips (31) can be used, as shown in FIGS. 17–18. The pericardial collar (30) of FIGS. 17–18 provides all of the above mentioned advantages and, furthermore, it decreases the stress on the chordae (3) by 50% through the attachment of the pericardial strips (31) shown in FIGS. 17–18.

The pericardial strips (31) are part of the same tissue used to create the pericardial collar (30). These strips (31) are attached to pericardial patch (5) with continuous and interrupted sutures (33), as shown in FIG. 18, to divide the stress load over more points. Thus, instead of the chordae (3) absorbing all the stress of attachment, these pericardial strips (31) absorb 50% of the stress, which leads to a more durable valve prosthesis. Strips (31) can be made from fabric. Suitable fabrics were described above with respect to collar (21). Fabric strips (31) can be a part of sewing collar (21) if collar (21) is made also from fabric. Alternatively, fabric strips (31) can be attached to collar (21), for example with suture.

The pericardial strips (31) are attached to the pericardial patch (5) and not the chordae (3), thus the chordal structure is not weakened. These strips are attached to the pericardial patch (5) and the chordal origin (8) so that the natural angulation and spatial geometry of the chordal origin (8) and chordae are maintained. The strips are the same length as the chordae of the valve prosthesis to maintain a uniform chordal tension and thus properly distribute the stress load between the strips and the chordae to increase the valve prosthesis' durability.

In the device of the present invention each individual chordae and chordal group (3) is preserved and naturally secured between mitral leaflets (6) and heterologous portions (8) of papillary muscle. These portions (8) of papillary muscle are affixed between two heterologous pericardial patches or synthetic materials using mono or polyfilament sutures, as shown in FIGS. 5–10. As shown in FIG. 4, the pericardial patches (5) are then sutured to the papillary muscle (4) of the patient. This procedure properly anchors the chordal groups to the papillary muscle (4), while respecting the spatial geometry and natural angulation of each chordae or chordal group (3). Further, a biological pericardial (21 or 30) collar can be sewn to the mitral sewing rim and this collar may further include various vertical heterologous strips (31) which are attached to the pericardial patch (5) to help distribute the stress of attachment.

This total biological device consists of a sewing collar (21 or 30), leaflets (6) and the subvalvular apparatus (2), having chordal attachments (3) which are naturally secured to their chordal origin (8), which is affixed to the pericardium (5) or to synthetic material and used as a heart valve substitute for the mitral and tricuspid valve of humans.

This device presents a specific design that allows the anchoring of it to the papillary muscle and mitral annulus of the patient, thus providing for better hemodynamic performance and avoiding disfunction and dilatation of the left ventricle. As a result thereof, this device benefits the recipient's quality of life as well as the durability of the device during use.

This heterologous total stentless mitral heart valve prosthesis may provide better durability, since it has all the known elements necessary for the harmonic function of the mitral valve and left ventricle which are not present in previous heart valve prostheses.

While in the foregoing specification a detailed description of an embodiment of the invention has been described for the purpose of illustration, many variations in the details herein given may be made by those skilled in the art without departing from the spirit and scope of the invention.

What is claimed is:

1. A heterologous total stentless mitral valve prosthesis obtained from a mammal with a size, anatomy and function similar to a human's, suitable for mitral and tricuspid valve replacement in a patient, the heterologous total stentless mitral valve prosthesis comprising:

a heart valve having an annulus, leaflets attached to said annulus and chordae extending from said leaflets, the annulus corresponding to the annulus of the valve obtained from said mammal and having a heterologous mitral sewing rim to be secured to the natural valve annulus of the patient; and a collar secured to said heterologous mitral sewing rim, such that said sewing rim is enveloped, to strengthen said mitral sewing rim.

2. The heterologous total stentless mitral valve prosthesis of claim 1 wherein said collar entirely envelopes said mitral sewing rim.

3. The heterologous total stentless mitral valve prosthesis of claim 1 wherein said collar comprises heterologous pericardial tissue.

4. A heterologous total stentless mitral valve prosthesis according to claim 1, wherein markings are placed on said collar at left and right trigone areas to determine a correct size of the valve.

5. A heterologous total stentless mitral valve prosthesis according to claim 1, wherein a mark is placed at the center of a weak posterior portion of said mitral sewing rim on said collar to provide a reference so that stress may be evenly distributed over said weak posterior portion during attachment of the mitral valve to the patient.

6. A heterologous total stentless mitral valve prosthesis according to claim 1, wherein said pericardial tissue is approximately 1 cm in width and has a length equal to a predetermined circumference of said mitral sewing rim, such that when it is secured to said mitral sewing rim approximately 50 mm of said collar are present on either side of said mitral sewing rim.

7. A heterologous total stentless mitral valve prosthesis according to claim 1, further comprising vertical stripes extending from said collar.

8. A heterologous total stentless mitral valve prosthesis according to claim 1, wherein said collar comprises heterologous pericardial tissue, said heterologous pericardial tissue including naturally secured vertical strips extending from said collar, and wherein said vertical strips have suitable size and placement for attachment to said patient's papillary muscle.

9. A method of selecting a heterologous total stentless mitral valve prosthesis of correct size for mitral or tricuspid valve replacement in humans, said heterologous mitral valve comprising a sewing rim to be secured to the natural valve annulus of the patient, the method comprising the steps of:

securing a collar to said sewing rim of said heterologous mitral valve to envelope said sewing rim;

placing markings on said collar at left and right trigone areas to determine correct size of the valve; and matching the intertrigonal area of the mitral annulus of the patient with a spacing between said markings to select a valve of correct size.

10. The method of claim 9 wherein said collar entirely envelopes said sewing rim.

11. The method of claim 9 wherein said collar comprises heterologous pericardial tissue.

12. The method of claim 9, further comprising the step of:

making a mark at the center of a weak posterior portion of said mitral sewing rim on said collar to provide a reference, so that stress may be evenly distributed over said weak portion during attachment of the mitral valve prosthesis to the patient.

* * * * *